United States Patent [19]  [11]  4,441,500
Sessions et al.  [45] * Apr. 10, 1984

[54] EKG ELECTRODE

[75] Inventors: Robert W. Sessions, Burr Ridge; Jerome Jeslis, Chicago; Richard A. Rodzen, Bolingbrook, all of Ill.

[73] Assignee: Ferris Manufacturing Corp., Hinsdale, Ill.

[*] Notice: The portion of the term of this patent subsequent to Oct. 12, 1999 has been disclaimed.

[21] Appl. No.: 247,560

[22] Filed: Mar. 25, 1981

Related U.S. Application Data

[63] Continuation-in-part of Ser. No. 141,057, Apr. 17, 1980, Pat. No. 4,353,373.

[51] Int. Cl.³ .............................................. A61B 5/04
[52] U.S. Cl. .................................................... 128/641
[58] Field of Search .............................. 128/639–641, 128/644, 783, 798, 803

[56] References Cited

U.S. PATENT DOCUMENTS

| 3,085,557 | 4/1963 | Berman et al. | 128/418 |
| 3,151,619 | 10/1964 | Sullivan | 128/417 |
| 3,487,827 | 1/1970 | Edmark | 128/2.06 |
| 3,701,346 | 10/1972 | Patrick, Jr. et al. | 128/641 |
| 3,805,769 | 4/1974 | Sessions | 128/2.06 |
| 3,828,766 | 8/1974 | Krasnow | 128/2.1 |
| 3,848,600 | 11/1974 | Patrick, Jr. et al. | 128/783 X |
| 3,989,035 | 11/1976 | Zuehlsdorff | 128/2.1 |
| 4,029,086 | 6/1977 | Corasanti | 128/2.06 |
| 4,034,854 | 7/1977 | Bevilacqua | 206/370 |
| 4,067,322 | 1/1978 | Johnson | 128/2.06 |
| 4,102,331 | 7/1978 | Grayzel et al. | 128/640 |
| 4,155,354 | 5/1979 | Rasmussen | 128/640 |
| 4,196,737 | 4/1980 | Bevilacqua | 128/798 |

FOREIGN PATENT DOCUMENTS 1965195 7/1971 Fed. Rep. of Germany ...... 128/640

Primary Examiner—Lee S. Cohen
Attorney, Agent, or Firm—Hill, Van Santen, Steadman & Simpson

[57] ABSTRACT

A circular EKG electrode has a plastic woven fabric body to which is attached a two-part connector. A jel impregnated disk is positioned over one part of the connector. The entire electrode is sealed in a disposable plastic package.

6 Claims, 15 Drawing Figures

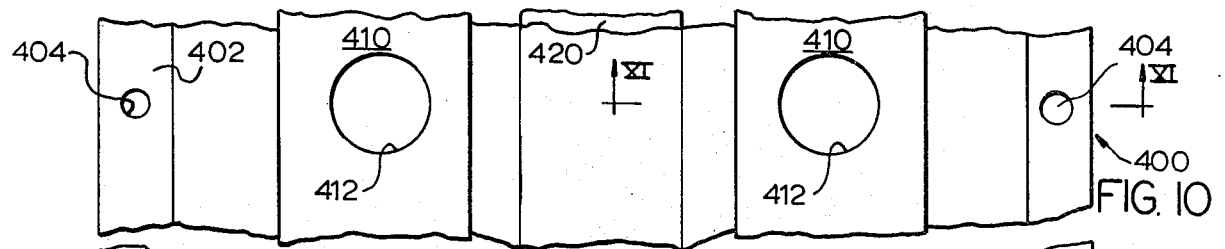
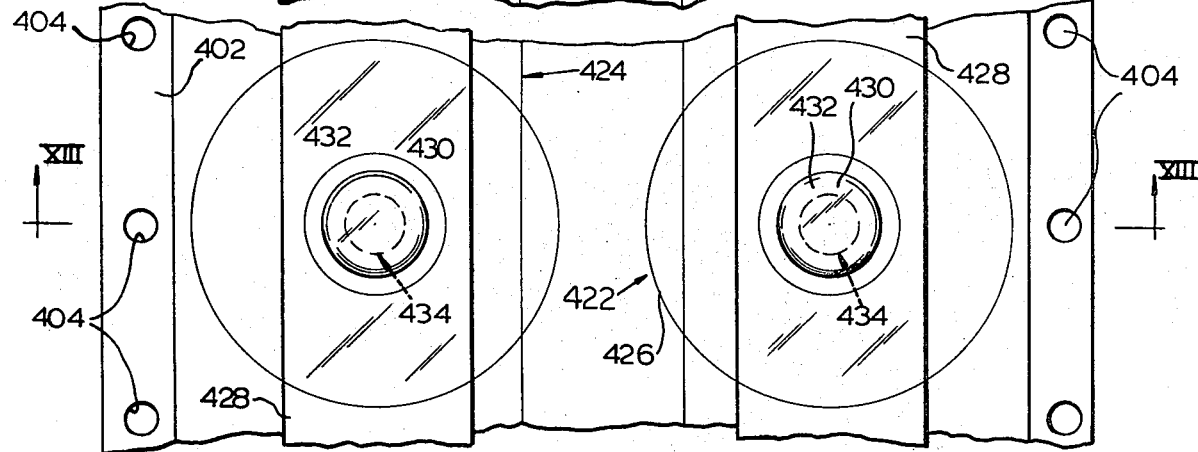
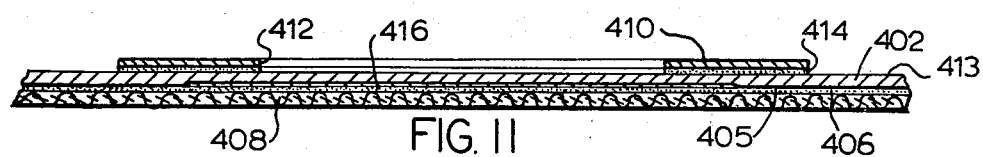
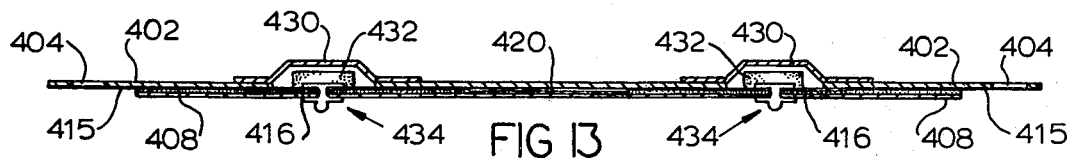
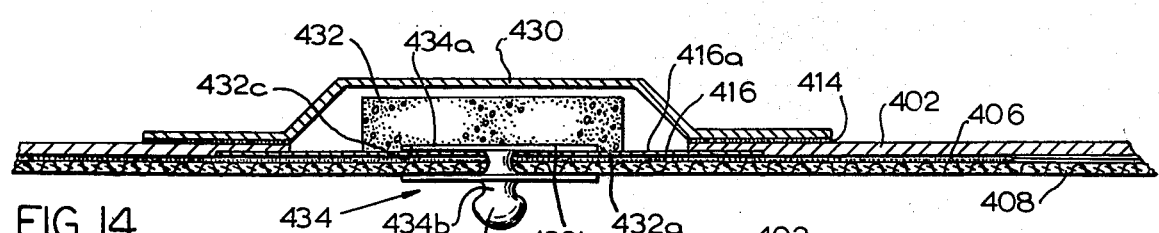
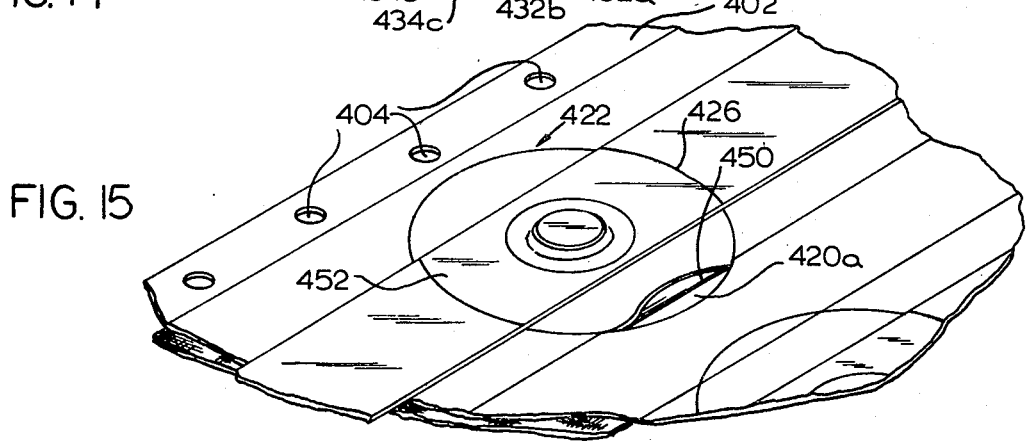

EKG ELECTRODE

CROSS REFERENCE TO RELATED APPLICATION

This application is a continuation-in-part of our copending application, United States Ser. No. 141,057, filed Apr. 17, 1980, now U.S. Pat. No. 4,353,373 and assigned to the same assignee of the present invention.

BACKGROUND OF THE INVENTION

1. Field of the Invention

The invention pertains to EKG electrodes and a method of making same.

2. Prior Art

EKG electrodes are well known in the prior art. Examples are found in U.S. Pat. No. 3,805,769 and U.S. Pat. No. 4,034,854. Many of the prior art EKG electrode structures, however, have suffered from the disadvantage that their shelf life has been measured in only weeks. One of the problems has been that the seal covering the disk of jel-impregnated foam in the electrode, which is adjacent the electrical contact, has not been adequate to retain the moisture in the jel for more than a few weeks of shelf life. Additionally, the prior art electrode structures have suffered from the defect that due to their size and circular shape, the number of them which could be used simultaneously on a person with a small chest has been limited.

SUMMARY OF THE INVENTION

Our present invention comprises an improved EKG electrode structure and associated package as well as a method of making same. The improved electrode structure has a rectangularly shaped foam pad with a layer of adhesive along one side thereof. Attached to the same side of the foam pad is a circular foam disk which has been impregnated with a jel. Adjacent the foam disk and extending through the rectangularly shaped foam pad is a metal electrical connector. The package of the electrode is formed with the adhesive side of the foam pad adhered to a thin layer of plastic such as polyethylene. The polyethylene has a circular hole in it through which extends the jelled disk. A plastic cap, polyethylene or MYLAR, is applied over the jelled disk and sticks to a layer of adhesive on the other side of the sheet of polyethylene. The plastic cap which is sealingly attached to the polyethylene base layer results in a very efficient form of packaging which extends the shelf life of the electrode from merely weeks to months.

Our inventive packaging may be formed with two strips of electrodes adhered to the base plastic layer, essentially parallel to one another. The polyethylene base layer may be folded in half, resulting in a very efficient and compact way in which to store the electrodes.

Our inventive method of forming our improved electrode and associated packaging starts with a multi-layer preform with a polyethylene sheet that has a series of holes. A plurality of rectangularly shaped foam pads is adhered to one side of the sheet due to the layer of adhesive on each of the pads. Each pad is centered with respect to a corresponding hole. On the other side of the polyethylene sheet is a layer of adhesive to which is temporarily attached a protective liner which has a series of holes therein. Each hole in the liner corresponds to a hole in the polyethylene sheet. A second liner is sealingly attached to the exposed adhesive on each of the foam pads to cover the series of holes in the foam pads. The method of forming our improved protective packaging along with our improved electrodes includes the steps of removing the second liner from the strip of pre-formed polyethylene material, making a hole through the foam pad essentially centered with respect to the hole in the first liner, applying a metal snap electrode through the hole in the foam pad, applying a centered foam disk to the adhesive layer on each pad adjacent the corresponding hole in the first liner, impregnating each of the foam disks with a jel, removing the first liner and applying a plastic cap over each of the impregnated foam disks. The plastic cap is sealingly adhered to the polyethylene sheet by a layer of adhesive on the polyethylene sheet.

In the above method, twice as many electrodes may be produced essentially simultaneously on a polyethylene or MYLAR sheet which is carrying two strips of rectangularly shaped EKG electrode pads by carrying out the above sequence of steps essentially simultaneously on both sets of electrode pads.

Another aspect of our invention includes a circular EKG electrode with a woven or spun plastic fabric lower layer removably adhered to a circular polystyrene base liner. A plastic cap is positioned over a hole in the polystyrene base liner. Under the plastic cap is positioned a cylindrical piece of jel impregnated foam and beneath that is a two-part eyelet and stud electrode which extends through a disk shaped piece of polyethylene and the spun lace poly electrode material. The jel impregnated cylindrical foam member is sealed between the plastic cap and the polyethylene label or disk which is affixed to the opposite side of the circular polystyrene base liner. The two-part eyelet and stud electrode extends through the polyethylene disk as well as the adjacent spun or woven plastic material.

Adjacent a portion of the spun lace poly material is a release liner which prevents that portion of the spun lace poly material from adhering to the circular polystyrene base liner.

BRIEF DESCRIPTION OF THE DRAWINGS

FIG. 10 is a fragmentary planar top view of a portion of an alternate laminated member.

FIG. 11 is a view in section taken along lines XI—XI of FIG. 10 disclosing the structure of the laminated member of FIG. 10.

FIG. 12 is a fragmentary top view of a pair of improved EKG electrodes formed in the laminated member of FIG. 10.

FIG. 13 is a view in section taken along the line XIII—XIII of FIG. 12 showing the structure of the electrodes of FIG. 12.

FIG. 14 is an enlarged fragmentary sectional view showing an enlarged portion of FIG. 13 and the details in section of an alternate improved EKG electrode.

FIG. 15 is a fragmentary perspective view showing an alternate EKG electrode cut from the laminated member of FIG. 10.

DETAILED DESCRIPTION OF THE PREFERRED EMBODIMENTS

Figure 1:
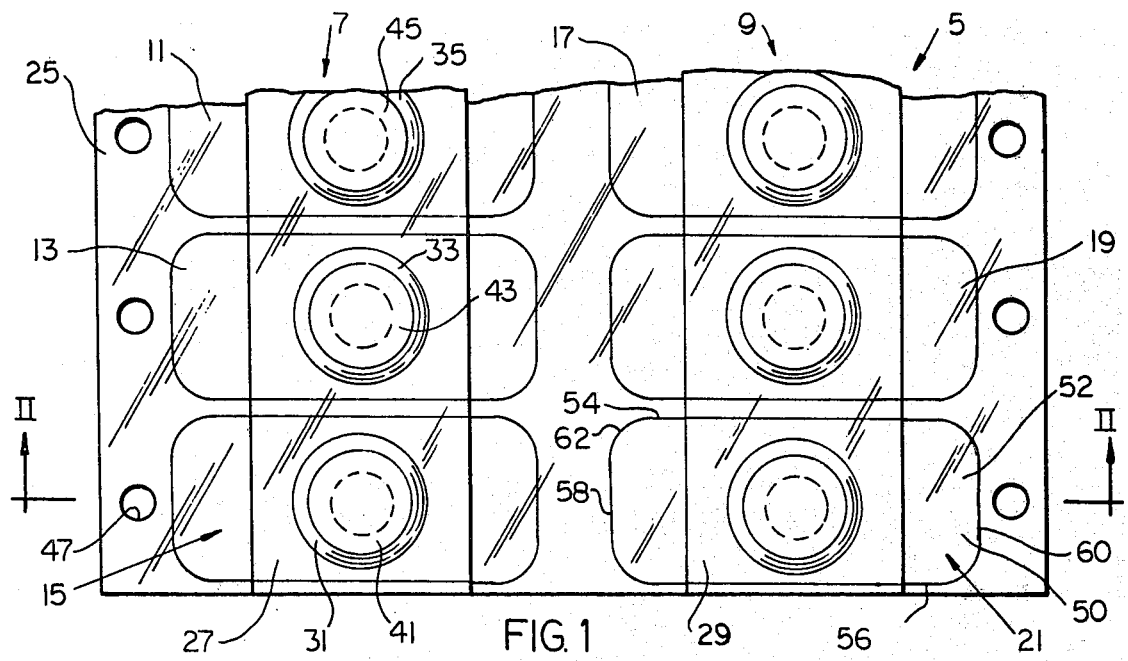
FIG. 1 is a planar top view showing two rows of electrodes sealed in our inventive package.
Figure 2:
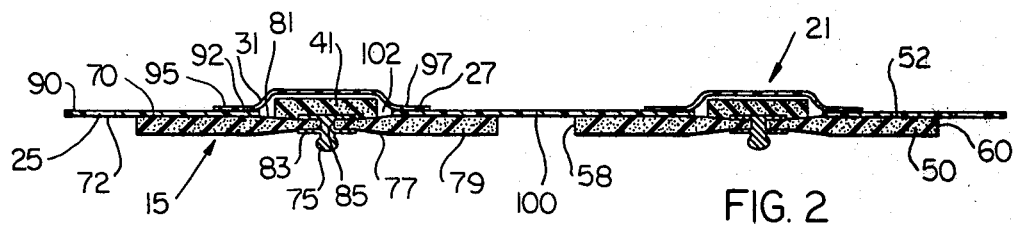
FIG. 2 is a sectional view taken substantially along the line II—II of FIG. 1.
Figure 3:
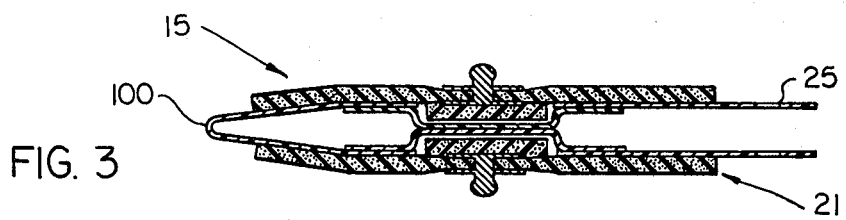
FIG. 3 is a sectional view showing the package of FIG. 2 folded in half.

Not by way of limitation, but by way of disclosing the best mode of practicing our invention, and by way of enabling one of ordinary skill to practice our invention, there is disclosed in FIGS. 1 through 3 one form of our invention, and in FIGS. 4 through 9 a method of practicing our invention.

FIG. 1 is a planar view of our improved EKG electrodes in associated packaging 5. Two parallel strips 7, 9 of our improved electrodes 11 through 21 are shown packaged and ready for use on a layer of liner material 25. The liner material 25 may be polyethylene or may be a MYLAR material. The MYLAR material is preferred because of its moistureretaining characteristics. Each of the electrodes 11 through 21 is removably attached to one side of the liner material 25. Attached to the other side of the linear material 25 are two parallel plastic strips 27, 29. The strips 27, 29 are sealingly bonded to the liner material 25. Each of the stripa 27, 29 includes a plurality of spaced apart cap members 31, 33, 35 which is formed in the polyethylene or MYLAR strip 27 or 29. Each of the cap members 31, 33 or 35 covers a foam disk such as the disks 41, 43 and 45. The sealing bond between the layer of plastic cover material 27 and the liner material 25 seals the moisture into the jel which has been injected into the foam disks 41 through 45 for a much longer period of time than has heretofore been possible. The moisture is further sealed into the jel due to the fact that each of the electrodes 11 through 15 is sealingly bonded to a lower side of the polyethylene liner sheet 25.

The polyethylene liner 25 is formed with a series of indexing holes 47 therein. Each of the holes 47 is spaced equidistant from an adjacent corresponding hole and may be used for indexing the liner sheet 25 along a manufacturing machine which is forming the package 5.

Each of the electrodes 11 through 21 is identical, and a description of the general shape of the electrode 21 will also describe the remaining electrodes 11 through 19. The electrode 21 is formed from a rectangularly shaped layer of medical foam 50. The layer of foam 50, approximately 1/16" thick, has an adhesive coated upper surface 52, and a pair of elongated spaced apart sides 54, 56. The elongated spaced apart sides 54, 56 are joined by a pair of shorter spaced apart sides 58, 60. Between each pair of sides 54, 58, for example, is a rounded corner 62. The elongated shape of the foam pad 50 makes it particularly suitable for close placement of the electrodes, or for use with persons that have a relatively small chest, such as children.

FIG. 2, a section taken substantially along the line II—II of FIG. 1, shows the structure of details of the packaging and the improved electrodes 5. On the left-hand side of FIG. 2, the electrode 15 which has an upper adhesive surface 70 is sealingly bonded to a lower surface 72 of the polyethylene liner 25. Centrally located with respect to the electrode 5 is a two-part metal contact 75 which extends from an outside surface 77 of the foam layer 79 through to an inside surface 81 of the foam layer 79. Adjacent both the outside surface and the inside surface, the metal contact 75 has an annular metal region 83 attached thereto. The metal contact 75 extends through a hole 85 in the foam layer 79. The two-part metal contact 75 when inserted from the top and bottom is pressed against the foam layer 79, compressing it and producing a moisture-resistant seal between the metal contact 75 and the foam material 79.

The jel impregnated disk 41 is sealingly bonded to the layer of adhesive 70 on the upper surface of the foam body 79 of the electrode 15. Additionally, the cap 31 is sealingly bonded to a top surface 90 of the polyethylene liner 25 by a sealing layer 92 which is applied to the top surface 90 of the polyethylene liner 25. The cap 31 is formed with a pair of laterally extending side members 95, 97 which sealingly adhere to the layer of adhesive 92. The electrode 15 is joined to the electrode 21 by a region 100 of the polyethylene liner 25. Except for the lateral displacement with respect to one another, electrodes 15 and 21 are identical.

As shown in FIG. 3, the electrode 15 may be folded over and moved adjacent to the electrode 21 by bending the region 100 of the polyethylene liner 25. The arrangement shown in FIG. 3 produces a very compact way in which the electrodes and associated packaging 5 may be stored on the shelf.

The advantage of the packaging arrangement shown in FIGS. 1 through 3 is that the caps, such as the cap 31 on the plastic strip 27 are sealingly bonded to the liner material 25 very effectively thus trapping the moisture in the jel in the disk 41. Additionally, the foam body 79 of each of the electrodes, such as the electrode 15, is sealingly bonded to the lower surface 72 of the liner 25, thus completing the seal and forming a region 102 wherein the moisture in the jel in the disk 41 is trapped and retained for a shelf life corresponding to several months. It should be noted that one aspect of our new package and electrode arrangement 5 is that each of the electrodes, such as the electrode 15 cooperates with the liner, such as the liner 25 and the sealing plastic layer 27 to produce the long term seal which retains the moisture in the electrode foam disk 41.

FIGS. 4 through 9 disclose the steps in the method of fabricating the electrode and packaging material 5.

Figure 9:
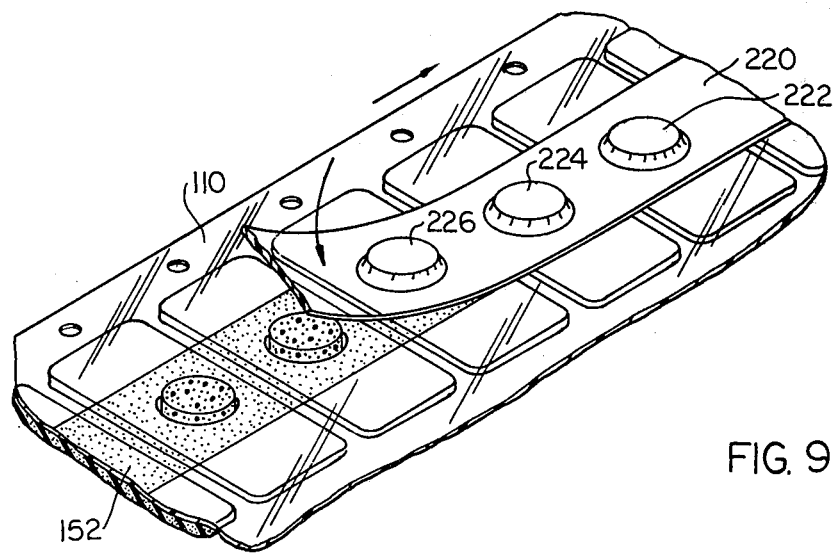
FIG. 9 is a perspective view of a fragmentary sheet of partially formed electrodes showing the step of applying a continuous, formed, plastic cover over each of the jelled disks previously applied to the strip of EKG electrodes.

In an initial step, a multi-layer pre-formed sheet 108 is prepared. This sheet includes a polyethylene base liner 110 corresponding to the previously discussed liner 25. Sealingly bonded to a lower side 112 of the polyethylene base liner 110 is a plurality of elongated foam members 114 through 122. Each of the foam members 114 through 122 corresponds to the previously discussed foam member 50. Centrally located with respect to each of the foam members 114 through 122 is a series of holes 124 through 132, a portion 134 through 142 of the upper adhesive layer of each of the elongated foam members 114 through 122 is exposed. The polyethylene base liner has an adhesive strip applied thereto on an upper surface 150. This elongated adhesive strip 152 clearly shown in FIG. 9, is initially protected by an elongated protective liner 154 applied to the top surface 150 of the member 110. The protective liner 154 has a set of holes such as a hole 156 which corresponds to the set of holes 124 through 132 in the polyethylene base liner 110. A second protective liner 158 is applied over the first protective liner 154 and temporarily adheres to the exposed adhesive regions 134 through 142 of the elongated foam strips 114 through 122.

Figure 4:
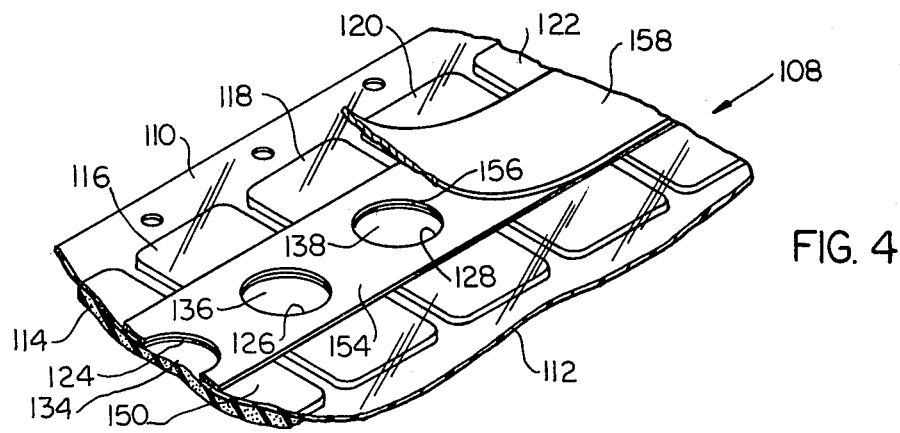
FIG. 4 is a perspective view of a fragment of the basic four-layer sheet material out of which our improved electrode and improved packaging material is formed.

Starting from the multi-layer pre-form 108 shown in FIG. 4, the next step of processing involves removing the outer protective liner 158.

Figure 5:
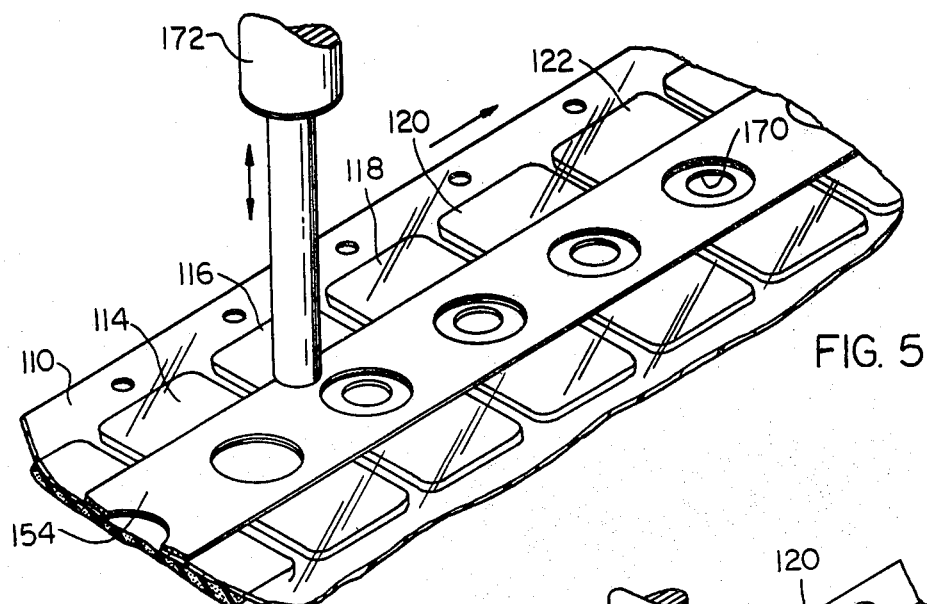
FIG. 5 is a perspective view of a fragment of the basic sheet material with a hole being punched through each EKG electrode pad.

As shown in FIG. 5, once the outer liner 158 is removed, a series of holes, such as a hole 170 may be punched through each of the foam members 114 through 122. Each of the holes such as the hole 170 is centered with respect to the previously formed holes 124 through 132 in the polyethylene base liner 110. Any conventional punching tool such as a tool 172 suitable for punching circular holes in foam material may be used to punch the holes 170.

Figure 6:
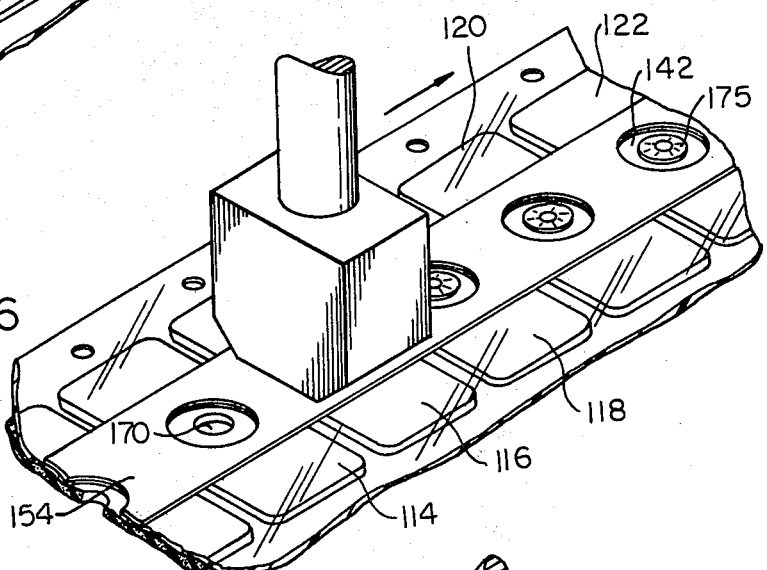
FIG. 6 is a perspective view of a fragment of the basic sheet material showing a metal contact being applied to each EKG electrode pad.

The next processing step as shown in FIG. 6, shows a two-part metal contact 175 corresponding to the contact 75 being applied to the holes, such as the hole 170 in the elongated piece of foam material such as the piece 114. Any type of one or two-part metal contact which can be applied from one side or both sides of each of the foam members 144 through 122 and which is suitable for connecting electrical instruments thereto may be used.

Figure 7:
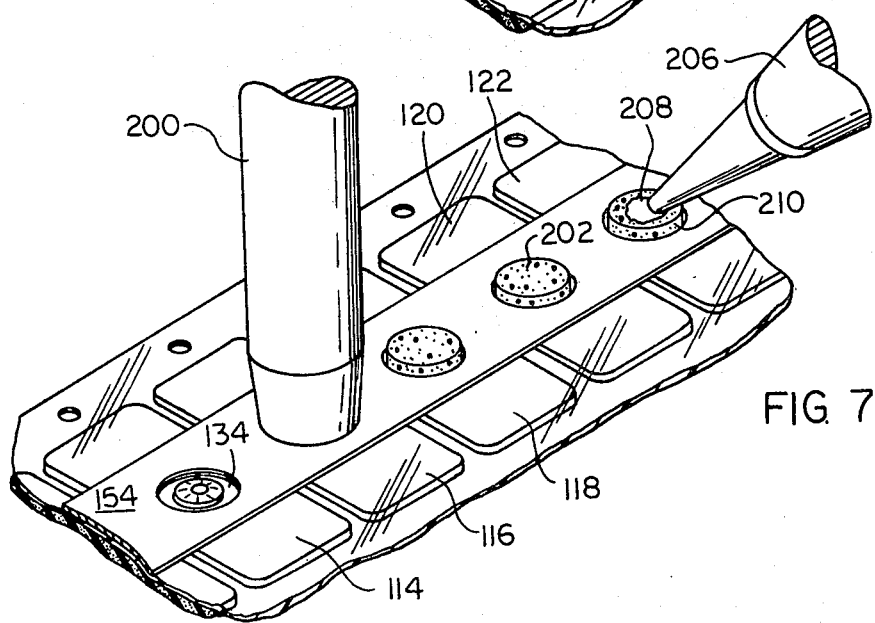
FIG. 7 is a perspective fragmentary view of a sheet of partially formed EKG electrodes showing the step of applying a foam disk to each electrode, adjacent one side of the metal contact, and the step of impregnating each said disk with jel.

FIG. 7 shows a tool 200 applying foam disks such as a foam disk 202 to each of the exposed adhesive regions 134 through 142 of each of the elongated foam members 114 through 122. FIG. 7 also shows a tool 206 injecting jel 208 into a foam disk 210 which had been previously applied to the annular adhesive region 142 left remaining once the connector 175 was applied to the elongated foam member 122. The foam disks 202, 210 adhere to the elongated foam members 114 through 122 due to the annularly shaped portion of the adhesive region 134 through 142 left exposed after the electrode contacts, such as the contact 175 have been applied to the elongated foam members 114 through 122.

Figure 8:
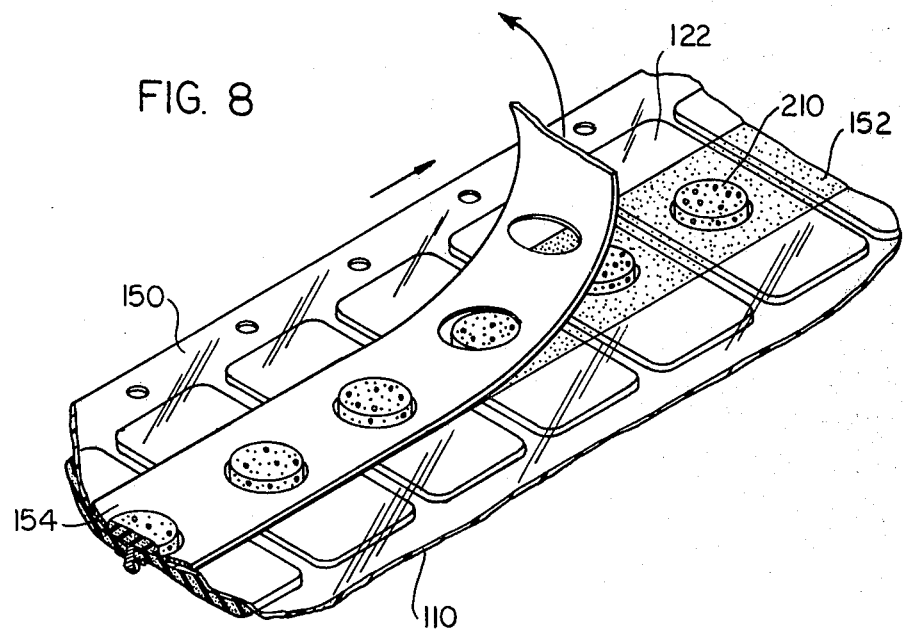
FIG. 8 is a perspective view of a fragmentary portion of a sheet of partially formed EKG electrodes showing the step of removing the remaining liner from the layer of polyethylene.

FIG. 8 shows a step of removing the protective liner 154 from the adhesive layer 152 on the top surface 150 of the polyethylene layer 110. Since the liner 154 has been removed after the jel has been applied by the applicator 206, the adhesive layer 152 has not been contaminated or otherwise damaged by the presence of any excess jel which might not have been injected completely into the disk 210.

In the last step of the process, shown in FIG. 9, a sealing layer of plastic, such as MYLAR, 220 having a plurality of caps 222 through 226 formed therein is sealingly applied to the layer of adhesive 152 and forms the remainder of the moisture proof seal with the polyethylene liner 110.

While our inventive method in FIGS. 4 through 9 has been shown being practiced with one strip of elongated foam members 114 through 122, it will be understood that the same method can be practiced with a double strip of foam members, corresponding to the structure 5 of FIG. 1.

Not only does the method shown between FIGS. 4 and 9 produce an improved packaging electrode structure 5, but because multiple rows of electrodes may be formed simultaneously, it is very inexpensive to form the electrodes and packaging 5 of our invention. The sheets of formed and packaged electrodes shown in FIG. 9 may then be cut apart as desired in the packages having predetermined numbers of electrodes. As can be seen with respect to FIG. 1, it will be appreciated that one of the advantages of our packaging arrangement 5 is that an electrode such as the electrode 21 may be readily removed from the liner 25 and conveniently used and no packaging material needs to be disposed of until all of the electrodes such as 11 through 21 have been removed from that particular piece of liner 25.

FIGS. 10 through 15 disclose an alternate form of our inventive electrode. In FIG. 10, a portion of a sheet of laminated stock 400 is shown which has a plastic base liner 402 formed of polystyrene, one example being of a size 5 mils by 6.5 inches wide, with a set of longitudinally arranged spacing holes 404 formed therein. FIG. 11, which is a sectional view taken along the line XI—Xi of FIG. 10, further illustrates the layered structure of the laminated member 400. Removably affixed to a lower side 405 of the base liner 402 by a layer of adhesive 406 is a layer of woven or spun plastic fabric 408 which will form a body portion of each completed electrode. We have found that an appropriate material is available under the trademark of FASSON S.C. SPUNLACE POLY. The layer of adhesive 406 between the base liner 402 and the woven or spun plastic fabric 408 is an acrylic adhesive. A pair of spaced apart release liners 410, each with a series of spaced apart holes 412, are affixed to a top surface 413 of the base liner 402 by layers of adhesive 414. The layers of adhesive 414 correspond to the adhesive layer 152 and are preferably an acrylic adhesive strip. FIG. 10 also discloses a release strip 420 which is positioned between the removable release liners 410. The release strip 420 is a paper release strip attached to the spun lace poly layer 408 by the layer of adhesive 406 and which has a red top surface. The release strip 420 does not adhere to the lower surface 405 of the base liner 402. The adhesive layer 406 can be partly embedded into openings in the plastic fabric 408.

FIG. 12 discloses a portion of the base liner 402 upon which a pair of electrodes 422, 424 have been formed. Each of the electrodes 422, 424 is formed with a circular periphery 426 when cut from the laminated member 400. In the view of FIG. 12, the release liners 410 have been replaced by plastic strips 428 of polyethylene or MYLAR in which are formed a series of spaced apart caps 430. Each cap 430 sealingly covers a cylindrically shaped piece of jel impregnated foam 432 which is positioned over a portion of an electrode 434. The strips 428 are attached to the surface 413 of base liner 402 by the adhesive strips 414.

FIG. 13 is a sectional view taken along the line XIII—XIII of FIG. 12, which shows the layered structure of the completed electrodes of FIG. 12. As can be seen from FIG. 13, the cylindrical, jel impregnated, foam member 432 is sealed by the cap 430, the base liner 402 and the circular polyethylene label or disk 416 which is adhesively and removably attached to the lower surface 405 of the base liner 402.

FIG. 14 is an enlarged fragmentary sectional view of a portion of FIG. 13. As can be seen from FIG. 14, a portion 432a of a planar end surface 432b of the cylindrically shaped jel impregnated piece of foam 432 is positioned on the polyethylene label or disk 416 and is affixed thereto by a layer of acrylic adhesive 416a. A remaining portion 432c of the planar surface 432b is adjacent a first part 432a of the electrode 434. The upper part 434a lockingly engages a lower part 434b to form the completed electrode. During assembly, the upper portion 434a and the lower portion 434b are applied from opposite sides of the base liner 402. The two parts 432a and 432b punch through the polyethylene layer 416 as well as the fabric layer 408 and lockingly engage one another as indicated in FIG. 14. In use, a stud 434c which has a generally spherical shape provides a point of electrical contact.

FIG. 15 discloses base liner 402 with the completed electrode 422 formed thereon. In FIG. 15, the periphery 426 has been cut disclosing the circular shape of the electrode 422 as well as a portion 420a of the release liner 420 which does not adhere to a portion 450 of the polystyrene body 452 bounded by the periphery 426.

When the electrode 422 is to be used, the disk shaped plastic fabric member 408 and the portion 420a of the release liner are manually separated from the polystyrene body 452. The disk shaped fabric 408 can then be pulled away from the plastic sealing body disk 452. When separated, the plastic disk 416 and jel impregnated foam 432 remain attached to the fabric member 408 along with the electrode 434. The layer of adhesive 406 which is embedded into the fabric 408 remains on the fabric 408 and is used to attach the fabric 408 to the patient. The plastic disk 452 is discarded.

An assembled electrode 422 has a long shelf life. The plastic liner or cover 452, the cap 430 and the adjacent disk 416 form a moisture retaining region. As a result, the jel impregnated foam cylinder 432 positioned therein will not dry out and become ineffective.

While various modifications and suggestions might be proposed by those skilled in the art, it will be understood that we wish to include all such modifications and changes within the claims of the patent warranted hereon as reasonably come within our contribution to the art.

We claim as our invention:

1. An improved EKG electrode comprising:
   an annular plastic base liner with a centrally located hole therein;
   a circular plastic disk removably attached to a first side of said base liner covering said hole;
   a circular plastic fabric member with a layer of adhesive on a first surface concentrically positioned with respect to said disk and attached thereto by said layer of adhesive, said fabric member is removably attached at said first surface to said first side of said base liner;
   means for electrical connection, said means extends at least through said circular plastic disk with a first portion located adjacent a first side of said disk, and essentially centered with respect to said hole in said base liner, and a second portion which extends outwardly from on opposite side of said circular plastic disk,
   a jel impregnated foam cylinder essentially centered with respect to said hole and extending in part therethrough with a planar end surface covering said first portion of said means for electrical connection, a part of said planar end surface is attached to a portion of said first side of said disk;
   a layer of adhesive formed on a second side of said base liner, said layer of adhesive extending continuously across said base layer from edge to edge thereof and surrounding said centrally located hole;
   a plastic cover with integrally formed planar sealing members, said planar sealing members are sealingly affixed to said second side of said base liner by said continuous layer of adhesive with said cover, said liner and said disk forming a sealed moisture retaining region such that said jel in said disk is prevented from drying out and hardening.

2. The improved EKG electrode according to claim 1, including further:
   a release liner adheringly affixed to a portion of said first surface of said fabric member adjacent a portion of said first side of said base liner such that said release liner and said attached portion of said fabric member can be manually and readily separated from said base liner in order to remove said base liner and said cover from said fabric member, said disk, said means for electrical connection and said jel impregnated cylindrical member.

3. An EKG electrode comprising:
   a circular moisture resistant flexible plastic disk,
   a flexible circular plastic body member with a layer of adhesive formed on one surface thereof,
   a jel impregnated foam cylinder,
   said moisture resistant flexible plastic disk is adheringly attached to said one surface of said flexible circular plastic body member,
   said jel impregnated foam cylinder is attached at an end to a part of a first surface of said circular moisture resistant flexible plastic disk,
   means for electrical connection, said means passes through at least said circular moisture resistant flexible plastic disk and has a conductive surface positioned adjacent a part of said end of said jel impregnated foam cylinder,
   a moisture resistant plastic base liner of a selected shape with a circular hole therethrough,
   a second layer of adhesive formed as a continuous strip on a first side of said plastic base liner surrounding said circular hole,
   moisture resistant means for covering having planar sealing regions, said planar sealing regions being in sealing contact with said second continuous layer of adhesive with a part of said moisture resistant means covering said hole in said plastic base liner,
   said assemblage of said flexible, circular plastic body member, said jel impregnated foam cylinder, said moisture resistant flexible plastic disk and said means for connection is removably attached to a second side of said moisture resistant plastic base liner by means of said layer of adhesive with a part of said jel impregnated foam cylinder positioned within said hole in said base liner such that a second end of said jel impregnated foam cylinder is positioned adacent a surface of said means for covering and such that a moisture retaining region is formed within which said jel impregnated cylinder is located, said region is bounded in part by a region of said means for covering and a region of said disk,
   said second layer of adhesive extends continuously on said first side of said plastic base liner completely across said plastic body member coextensive with at least a selected diameter of said circular plastic body member.

4. The EKG electrode according to claim 3 including further,
means for releasing, said means is adapted to be used to manually separate said plastic base liner from said circular plastic body member.

5. In a plurality of circular EKG electrodes removably formed along a line on a first side of a plastic base liner wherein a plurality of holes is formed in the base liner along the line, each electrode includes a body portion with an electrical connector affixed thereto and a jel impregnated foam cylinder with an end positioned adjacent a part of the electrical connector, each jel impregnated foam cylinder is positioned to extend in part through a respective one of the holes in the base liner, an improvement comprising:
a continuous strip of adhesive formed on an opposite side of the plastic base liner along the line, said strip of adhesive surrounds the members of the plurality of holes formed in the base liner along the line, and
continuous plastic means for covering, said means for covering is continuously and sealingly bonded by said continuous strip of adhesive to said opposite side of the base liner thereby forming a plurality of moisture retaining regions wherein the members of the plurality of foam cylinders are located, each said moisture retaining region is bounded by a part of said base liner, a part of said means for covering and a part of the circular electrode.

6. In a circular EKG electrode removably attached to a first side of a plastic base liner wherein the plastic base liner has a hole formed therein, the electrode includes a body portion with an electrical connector affixed thereto and a jel impregnated foam cylinder with an end positioned adjacent a part of the electrical connector, a part of the cylinder extends into the hole in the base liner, an improvement comprising:
a continuous layer of adhesive formed on an opposite side of the plastic base liner, said continuous layer of adhesive extends along a diameter from edge to edge of the circular EKG electrode and surrounds the hole in the base liner, and
moisture resistant means for covering, said means for covering is sealingly and continuously bonded to said opposite side of the plastic base liner by said continuous layer of adhesive, said means for covering includes planar sealing members which extend at least along the diameter to said edges of the electrode and cover completely said layer of adhesive such that a moisture retaining region is formed wherein the foam cylinder is located, said moisture retaining region is bounded by a part of said means for covering, a part of the base liner, and a part of the circular electrode.

* * * * *